(12) United States Patent
Araki et al.

(10) Patent No.: US 7,033,994 B2
(45) Date of Patent: Apr. 25, 2006

(54) MEDICINAL COMPOSITIONS FOR PREVENTING AND TREATING HEMORRHAGIC DISEASES ASSOCIATING THROMBOPATHY

(75) Inventors: Tatsuya Araki, Kumamoto (JP);
Kazuhiko Tomokiyo, Kumamoto (JP);
Yasushi Nakatomi, Kumamoto (JP);
Kaori Teshima, Kumamoto-ken (JP);
Tomoko Watanabe, Kumamoto-ken (JP); Tomohiro Nakagaki, Kumamoto-ken (JP)

(73) Assignee: Juridical Foundation the Chemo-Sero-Therapeutic Research Institute

( * ) Notice: Subject to any disclaimer, the term of this patent is extended or adjusted under 35 U.S.C. 154(b) by 296 days.

(21) Appl. No.: 10/168,727

(22) PCT Filed: Dec. 21, 2000

(86) PCT No.: PCT/JP00/09101

§ 371 (c)(1),
(2), (4) Date: Aug. 21, 2002

(87) PCT Pub. No.: WO01/47547

PCT Pub. Date: Jul. 5, 2001

(65) Prior Publication Data

US 2003/0125250 A1    Jul. 3, 2003

(30) Foreign Application Priority Data

Dec. 24, 1999  (JP)  ................... 11-368123
Dec. 24, 1999  (JP)  ................... 11-368124

(51) Int. Cl.
*A61K 38/00* (2006.01)
*A61K 35/14* (2006.01)
*A61K 35/16* (2006.01)

(52) U.S. Cl. .................. 514/2; 514/802; 514/834; 530/350; 530/380

(58) Field of Classification Search .................. 514/2, 514/802, 834; 530/350, 380
See application file for complete search history.

(56) References Cited

U.S. PATENT DOCUMENTS

| 4,994,438 | A |   | 2/1991  | Rubinstein   | 514/2    |
|-----------|---|---|---------|--------------|----------|
| 5,180,583 | A |   | 1/1993  | Hedner       | 424/94.64|
| 5,252,710 | A |   | 10/1993 | Dazey et al. | 530/383  |
| 5,618,789 | A |   | 4/1997  | Capon et al. | 514/12   |
| 5,760,183 | A | * | 6/1998  | Dazey et al. | 530/383  |

FOREIGN PATENT DOCUMENTS

| EP | 774261 A2     | 5/1997  |
| WO | EP 0 225 160 A2 | 6/1987 |
| WO | EP 0 469 985 A1 | 2/1992 |
| WO | 98/53848 A1   | 12/1998 |

OTHER PUBLICATIONS

Dickneite et al. Reduction of r-hirudin induced bleeding in pigs by the administration of von Willebrand factor. (1996) Platelets, vol. 7, pp. 283-290.*
Furlan et al. Von Willebrand Factor in Thrombotic Thrombocytopenic Purpura. (1999) Thromb. Haemost. vol. 82, No. 2, pp. 592 600.*
English Translation of Schwarz et al. EP 0 774 261.*
Schwarz et al. Evaluation of recombinant von Willebrand factor in a canine model of von Willebrand disease. (1998) Haemophilia, vol. 4, (Supp. 3) pp. 53-62.*
J. Nishimura, Progress of Medicine, vol. 184, pp. 448-452, 1998.
Y. Kurata, Sogo Rinsho, vol. 47, pp. 2742-2748, 1998.
Ministry of Health and Welfare, Pharmaceutical Affairs Bureau; the Japanese Red Cross Society: As to proper use of platelet preparations.
P.J. Fay et al.; J. Biol. Chem., vol. 226, No. 4, pp. 2172-2177, 1991.
D. Eaton et al.; Biochemistry, vol. 25, pp. 505-512, 1986.
Z.M. Ruggeri et al.; J. Clin. Invest. vol. 99, No. 4, pp. 559-564, 1997.
F. Rotblat et al., Biochemistry, vol. 24, pp. 4294-4300, 1985.
H. J. Weiss et al.; Science, vol. 182, pp. 1149-1151, 1973.
C. A. Fulcher et al.; Proc. Natl. Acad. Sci. USA, vol. 79, pp. 1648-1652, 1982.
D. J. Kuter et al.; Blood, vol. 85, No. 10, pp. 2720-2730, 1995.
Mauz-Koerhølz et al., Arch Dis Child, vol. 78, pp. 257-260 (1998).

* cited by examiner

*Primary Examiner*—Robert A. Wax
*Assistant Examiner*—Holly Schnizer
(74) *Attorney, Agent, or Firm*—Birch, Stewart, Kolasch & Birch, LLP

(57) ABSTRACT

The present invention provides a pharmaceutical composition for treatment and prevention of bleeding disorders caused by platelet disorders, not caused by defect in blood coagulation factors or von Willebrand Factor but caused by reduction of circulating platelet count or platelet dysfunction, said composition comprising a hemostatic effective amount of Factor VIII and/or von Willebrand Factor. Also provided is a method for treating said bleeding, comprising administering a hemostatic effective amount of Factor VIII and/or von Willebrand Factor to patients suffering from bleeding disorders caused by platelet disorders.

2 Claims, 2 Drawing Sheets

Blood loss is shown in mean ± standard error.

\* ; $p<0.05$, vs saline (student's t-test)
\*\*; $p<0.01$, vs saline (student's t-test)
\# ; $p<0.05$, vs FVIIa (student's t-test)

Blood loss is shown in mean ± standard error.
* ; p<0.05, vs saline (student's t-test)

MEDICINAL COMPOSITIONS FOR PREVENTING AND TREATING HEMORRHAGIC DISEASES ASSOCIATING THROMBOPATHY

This application is the national phase under 35 U.S.C. §371 of PCT International Application No. PCT/JP00/09101 which has an International filing date of Dec. 21, 2000, which designated the United States of America.

TECHNICAL FIELD OF THE INVENTION

The present invention relates to a medicament for treating bleeding disorders caused by platelet disorders such as, for example, thrombocytopenia and platelet dysfunction. More particularly, the present invention relates to a medicament for treatment and prevention of bleeding disorders caused by platelet disorders, comprising Factor VIII (hereinafter also referred to as "FVIII") and/or von Willebrand Factor (hereinafter also referred to as "vWF") as an active ingredient.

BACKGROUND OF THE INVENTION

Hemostasis is achieved by blood vessel, platelets and blood coagulation factors that function normally. Reduced function of any of these elements enhances bleeding and extraordinary functional reduction induces excess bleeding to such an extent that life is even threatened.

Platelets, present in blood at 130,000 to 360,000/µL, promptly cluster around wounded portions of blood vessel to play an important role in hemostasis. When hemostatic function of platelets does not work normally or the number of circulating platelets is reduced (less than 50,000/µL) by some causes, bleeding is enhanced. In severe cases (less than 10,000/µL), bleeding is induced even spontaneously and thereby excess bleeding might threaten life. Thrombocytopenia caused by anti-cancer chemotherapy, which goes on increasing in recent years, is serious side effect. How to control bleeding disorders caused by thrombocytopenia is an important problem in treating cancer (J. Nishimura, Progress of Medicine 184: 448–452, 1998).

Principally, thrombocytopenia is divided into four classes in view of mechanism. The first class is caused by decrease in platelet production in bone marrow, including aplastic anemia, hematopoietic suppression in bone marrow after administration of anti-cancer agents, and alteration for normal hematopoietic organ as in acute leukemia. The second class is due to promotion of platelet destruction by anti-platelet antibody, including idiopathic thrombocytopenic purpura (ITP). This class also includes thrombocytopenia induced by drug allergy and newborn thrombocytopenia caused by unfit platelet blood type pregnancy. The third class is caused by accelerated consumption of platelets including disseminated intravascular coagulation (DIC) and thrombotic thrombocytopenic purpura (TTP) wherein a large number of platelets is consumed at peripheral thrombopoietic sites to induce thrombocytopenia. Finally, the fourth class is due to abnormal distribution of platelets. In normal adults, platelets newly produced in bone marrow are peripherally released but about one third thereof is captured at the spleen without peripheral circulation. In case of hepatocirrhosis or splenomegalia, however, most of newly produced platelets are captured at the spleen. Consequently, in spite of platelet production in bone marrow, platelets are not sufficiently provided to peripheral circulation to thereby induce thrombocytopenia (Y. Kurata, Sogo Rinsho 47: 2742–2748, 1998). For platelet dysfunctions, thrombasthenia caused by deficiency of platelet membrane glycoproteins (GP) IIb/IIIa and Bernard-Soulier's syndrome caused by deficiency of GP Ib are known.

Hemostatic disorders caused by platelet disorders cause enhanced bleeding as shown by mucosal hemorrhage in a nose-mouse area and the gastrointestinal tract as well as exudation from wound, ulcer or injected site. Bleeding in thrombocytopenia is extensive and hence thrombocytopenia is a serious problem both during and after surgical operation. When the number of platelets is reduced as low as 50,000/µL or less, serious bleeding is likely to occur even in a minute surgical operation such as a tooth extraction. Further reduction in the number of platelets to as low as 10,000/µL or less might induce spontaneous bleeding in the absence of specific events such as surgical operation or trauma wherein intracranial hemorrhage might often be lethal.

Currently, transfusion of platelet concentrates is only clinically efficacious treatment for bleeding caused by thrombocytopenia or platelet dysfunction. In practice, platelet concentrates is basically administered so that there may be attained 50,000/µL or more of platelets in case of surgical operation or active bleeding or 20,000/µL or more of platelets in other cases (Ministry of Health and Welfare, Pharmaceutical Affairs Bureau; the Japanese Red Cross Society: As to proper use of platelet preparations).

However, when the platelet concentrates are administered frequently in a large amount, platelets derived from multiple blood donors are used. As a consequence, many patients who repeatedly received platelet transfusion will come to produce an isoantibody to HLA antigens of contaminated leukocytes, platelet blood-type antigens of platelets or membrane proteins of platelets and become incapable of platelet transfusion due to attenuated effects of transfusion. Moreover, possibility is not utterly denied that the platelet concentrates are contaminated with lymphocytes causative of post-transfusion GVHD or viruses that cause hepatitis or AIDS. Besides, shortage of supply is likely to occur since the platelet concentrates can effectively be used for as short as 3 to 5 days. Accordingly, there is an earnest desire for a medicament that is safe, easy to manage hemostasis and capable of storage, in place of platelet transfusion that is currently the only treatment for bleeding disorders caused by thrombocytopenia or platelet dysfunction.

DISCLOSURE OF THE INVENTION

Under the circumstances, the present inventors have investigated in order to develop a medicament for treatment and prevention of bleeding disorders caused by platelet disorders. As a result, it has surprisingly been found that purified FVIII and/or vWF, which has never been attempted hitherto, could improve lowered hemostatic ability of thrombocytopenic animals when they were administered within the living body. In view of this, the present inventors expected that FVIII and/or vWF could be used as a medicament for treatment and prevention of bleeding caused by thrombocytopenia or platelet dysfunction to thereby complete the present invention.

BEST MODE FOR CARRYING OUT THE INVENTION

Figure 1:
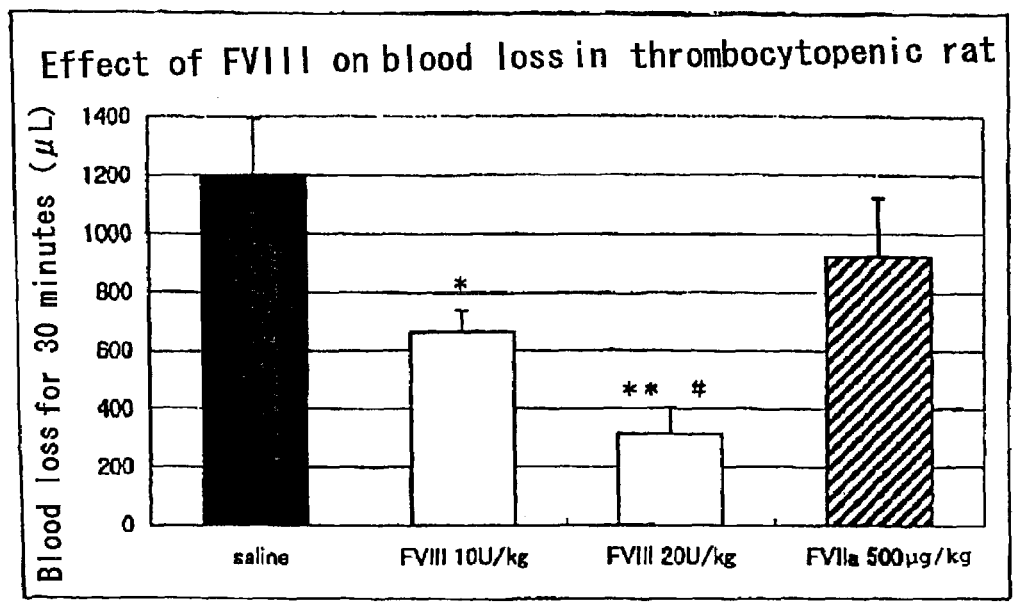
FIG. 1 is a graph showing effects of the pharmaceutical composition of the present invention containing Factor VIII in thrombocytopenic animals.

FVIII is primarily synthesized in the liver and present in plasma at 0.1 μg/mL, which level is the lowest among the blood coagulation factors. In circulation, FVIII forms a complex with vWF to protect from proteolysis by proteases such as activated Protein C (Fay, P. J. et al., J. Biol. Chem. 266: 2172–2176, 1991). Congenital deficiency of FVIII is known as hemophilia A with symptoms of serious bleeding due to blood coagulation disorders. Concentrated preparations of FVIII derived from blood or prepared by the genetic recombinant technique has been used for hemostatic management of hemophilia A patients.

FVIII functions not as a protease but as a cofactor in the coagulation pathway and has an activity to extremely enhance a catalytic rate of limited hydrolysis (activation) of Factor X by activated Factor IX. FVIII consists of the following domains: "A1" (amino acids 1 to 329) homologous to Factor V or ceruloplasmin; "A2" (amino acids 380 to 711); "A3" (amino acids 1640 to 2019); "C1" (amino acids 2020 to 2172) homologous to discoidin lectin; "C2" (amino acids 2173 to 2332); and "B" (amino acids 712 to 1648) domains. FVIII also contains two acidic sequences, called "a1" (amino acids 331 to 372) and "a2" (amino acids 1649 to 1689), the latter functioning as a binding site for vWF. The cofactor activity of FVIII is elicited when free FVIII is formed after release of the bound vWF via limited proteolysis by thrombin and is enhanced when Arg372-Ser373 bondage within the molecule is cleaved by limited proteolysis (Eaton, D. et al., Biochemistry 25: 505–512, 1986).

vWF is present as a giant multimeric molecule with a molecular weight of 500,000 to as high as 20,000,000, wherein two to several ten single subunits, each subunit being consisted of 2050 amino acid residues with a molecular weight of about 250,000, are bound together. vWF interacts at its distinct recognition sites with various kinds of collagen under the endothelium. Once bound with collagen, vWF changes its steric structure through shear stress so that a binding site for platelet GPIb is exposed to thereby bind to platelets (Ruggeri, Z. M. et al., J. Clin. Invest. 99: 559–564, 1997).

While platelets are rolling on vWF immobilized on collagen, platelet adhesion occurs by formation of strong binding between platelet GPIa-IIa and collagen under the endothelium or between activated platelet GPIIb/IIIa and adhesive proteins under the endothelium via RGD sequence in vWF or fibronectin. It is also known that vWF plays an important role in further platelet aggregation. In any way, vWF plays an important role in platelet adhesion and aggregation through functioning as an adhesive molecule between collagen of the wounded blood vessel wall and platelets or between platelets themselves. Accordingly, vWF deficient patients (von Willebrand's disease) manifest bleeding due to failure of platelet adhesion and aggregation. Besides, vWF also acts as a carrier protein for FVIII in circulating blood.

FVIII and vWF as used herein may be prepared by any method known in the art including isolation from human blood or with the use of the genetic recombination technique. FVIII and vWF for use in the present invention are preferably purified.

FVIII may be prepared from blood by the following methods. For example, it may be prepared by purifying FVIII from cryoprecipitate, obtained by thawing of fresh frozen human plasma at low temperature, by affinity chromatography using a column with anti-vWF monoclonal antibody or anti-FVIII monoclonal antibody (Rotblat, F. et al., Biochemistry 24: 4294–4300, 1985).

On the other hand, vWF may be prepared from blood by the following methods. For example, it may be prepared by purifying vWF/FVIII complex from cryoprecipitate, obtained by thawing of fresh frozen human plasma at low temperature, by cation exchange chromatography, followed by gel filtration with a high salt concentration to isolate vWF (Weiss, H. J. et al., Science 182: 1149–1151, 1973), or by affinity chromatography using anti-vWF monoclonal antibody to purify vWF (Fulcher, C. A. et al., Proc. Natl. Acad. Sci. USA 79: 1648–1652, 1982).

Each of the thus prepared FVIII and/or vWF may be stored by freeze-drying with appropriate stabilizing agents to ensure maintenance of the activity of FVIII and/or vWF at maximum level. Alternatively, a solution of FVIII and/or vWF may be frozen for storage. In accordance with the present invention, FVIII and/or vWF as an active ingredient is combined with a suitable excipient known in the art to formulate a medicament for treatment and prevention of bleeding disorders caused by platelet disorders.

The medicament of the present invention may be administered to any patients who suffer from bleeding disorders caused by thrombocytopenia or platelet dysfunction.

Although an effective dose of FVIII may vary depending on, for example, age of patient, symptoms and severity of diseases, hemostatic effect is anticipated with FVIII at 5 to 400 U/kg (body weight), preferably at 50 to 100 U/kg (body weight) based on FVIII clotting activity. FVIII may most suitably administered with single administration (Bolus) or by intravenous drip injection.

As for vWF, although its effective dose may vary depending on, for example, age of patient, symptoms and severity of diseases, hemostatic effect is anticipated with vWF at 10 to 400 U/kg (body weight) based on ristocetin cofactor (Rcof) activity in a dose-dependent manner. vWF may most suitably be administered with single administration (Bolus) or by intravenous drip injection.

For use of FVIII and/or vWF as treatment and prevention of bleeding disorders caused by platelet disorders, either FVIII or vWF may be administered each alone or in combination thereof or alternatively FVIII/vWF complex may be administered with sufficient efficacy.

The present invention is explained in more detail by means of the examples mentioned below.

PREPARATION EXAMPLE

Cryoprecipitate is prepared by thawing fresh frozen human plasma at low temperature, and after dissolving, is subject to cation exchange chromatography and precipitation fractionation to purify FVIII/vWF complex. Then, gel filtration was performed in the presence of 350 mM calcium chloride with Sephacryl S-500 to dissociate FVIII and vWF from each other and each FVIII and vWF was isolated.

EXAMPLE

The following Examples proved hemostatic effect of FVIII and/or vWF administration to bleeding caused by thrombocytopenia.

Example 1

Effect of the Pharmaceutical Composition of the Present Invention (Containing Factor VIII) by Thrombocytopenic Animal Model:

This example was performed with the model established as showing thrombocytopenia caused by administration of anti-cancer agent (Kuter, D. J. et al., Blood 85: 2720–2730, 1995). The model used is considered to be suitable for the evaluation of bleeding caused by thrombocytopenia. Male Wistar rats weighing 180 to 230 g received subcutaneously anti-cancer agent "Busulfan" (trade name) at 12.5 mg/kg at the back to induce thrombocytopenic conditions. On day 14 when the platelet count reached minimum, the animals were anesthetized with pentobarbital, fixed at the dorsal position, and cut at a site of tail with 3 mm diameter with a cutter blade to allow bleeding. Blood discharged was absorbed to filter and a volume of blood loss was determined and estimated by hemoglobin quantification. While the volume of blood loss was 112.2±61.0 μL in normal rat having about 600,000 μL of platelets, blood loss was enhanced as the platelet counts were reduced in the test animals and was as high as 1202.8±188.3 μL when the platelet counts were reduced to 1,000±1,000/μL.

Rats were made thrombocytopenic and received human FVIII, which was genetic recombinant FVIII ("KOGENATE" (trade name) manufactured by BAYER Pharmaceuticals) and administered at 10 and 20 U/kg based on clotting activity via the outer cervix vein ten minutes prior to beginning of estimation. Similarly, human FVIIa was administered at 500 μg/kg and estimated. The results are summarized in Table 1 and FIG. 1.

Blood loss in thrombocytopenic rats was remarkably lowered after administration of FVIII in a dose dependent manner as compared to control animal. Among animals administered with FVIII at 20 U/kg, one animal manifested complete hemostasis within 30 minutes observation and blood loss as low as normal rat. Reduction of blood loss was also observed in the group administered with a high dose of FVIIa (500 μg/kg), hemostatic effect of which is disclosed in Japanese Patent Publication No. 80783/1995. However, the hemostatic effect of FVIII administration surpassed the effect of FVIIa.

TABLE 1

| Group | No. of animals | No. of animals with hemostasis within 30 min. | Mean volume of blood loss (μl) |
|---|---|---|---|
| Control* | 5 | 0 | 1202.8 |
| FVIII 10 U/kg | 4 | 0 | 662.7 |
| FVIII 20 U/kg | 4 | 1 | 311.5 |
| FVIIa 500 μg/kg | 4 | 0 | 924.2 |

*Physiological saline

Example 2

Effect of the Pharmaceutical Composition of the Present Invention (Containing von Willebrand Factor) by Thrombocytopenic Animal Model:

This example was performed as described in Example 1.

Figure 2:
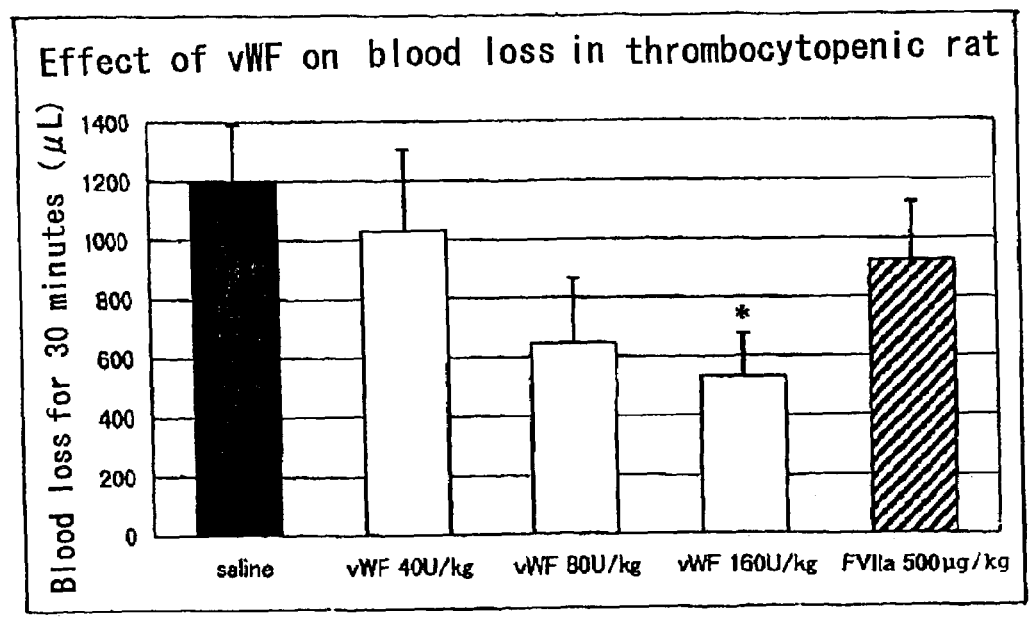
FIG. 2 is a graph showing effects of the pharmaceutical composition of the present invention containing von Willebrand Factor in thrombocytopenic animals.

Rats were made thrombocytopenic (platelet level: 1,000±1,000/μL) and human vWF was administered at 40, 80 and 160 U/kg based on Rcof activity via the outer cervix vein ten minutes prior to beginning of estimation. Similarly, human FVIIa was administered at 500 μg/kg and estimated. The results are summarized in Table 2 and FIG. 2.

Blood loss in thrombocytopenic rats was remarkably lowered after administration of vWF in a dose dependent manner as compared to control animal. In about a half of animals administered with vWF, complete hemostasis was observed within 30 minutes. Reduction of blood loss was also observed in the group administered with a high dose of FVIIa (500 μg/kg), hemostatic effect of which is disclosed in Japanese Patent Publication No. 80783/1995. However, the hemostatic effect of vWF administration surpassed the effect of FVIIa.

TABLE 2

| Group | No. of animals | No. of animal with hemostasis within 30 min. | Mean volume of blood loss (μl) |
|---|---|---|---|
| control* | 5 | 0 | 1202.8 |
| vWF 40 U/kg | 4 | 1 | 1030.4 |
| vWF 80 U/kg | 4 | 2 | 644.2 |
| vWF 160 U/kg | 4 | 2 | 528.4 |
| FVIIa 500 μg/kg | 4 | 0 | 924.2 |

*Physiological saline

What is claimed is:

1. A method for treating bleeding disorders, comprising administering a hemostatic effective amount of von Willebrand Factor to patients suffering from bleeding disorders, wherein said bleeding is caused by thrombocytopenia, thrombasthenia caused by deficiency of platelet membrane glycoproteins (GP) IIb/IIIa, or Bernard-Souler's syndrome caused by deficiency of GP Ib, but said bleeding is not caused by a defect in blood coagulation factors or in von Willerbrand Factor.

2. The method of claim 1, wherein 10 to 400 U/kg (body weight) of von Willebrand Factor based on ristocetin cofactor activity is administered.

* * * * *